United States Patent [19]
Thong et al.

[11] Patent Number: 5,955,065
[45] Date of Patent: Sep. 21, 1999

[54] ANTIPERSPIRANT COMPOSITIONS CONTAINING CALCIUM SALTS

[75] Inventors: Stephen Hong-Kwee Thong, Needham, Mass.; Teresa M. Weber, Bethesda, Md.; Kristina N. Prodouz, Boston, Mass.

[73] Assignee: The Gillette Company, Boston, Mass.

[21] Appl. No.: 09/136,770

[22] Filed: Aug. 19, 1998

[51] Int. Cl.$^6$ .............. A61K 7/38; A61K 7/34; A61K 7/32; A61K 7/00
[52] U.S. Cl. .............. 424/68; 424/65; 424/66; 424/400; 424/401
[58] Field of Search .............. 424/68, 65, 66, 424/400, 401

[56] References Cited

U.S. PATENT DOCUMENTS

| | | | |
|---|---|---|---|
| 2,350,047 | 5/1944 | Kiarmann et al. | 167/90 |
| 2,571,030 | 10/1951 | Govett et al. | 167/90 |
| 3,979,510 | 9/1976 | Rubino | 424/47 |
| 3,996,346 | 12/1976 | Staffier et al. | 424/67 |
| 3,998,788 | 12/1976 | Rubino | 424/47 |
| 4,017,599 | 4/1977 | Rubino | 424/47 |
| 4,021,536 | 5/1977 | Rubino | 424/47 |
| 4,526,780 | 7/1985 | Marschner et al. | 424/66 |
| 4,659,560 | 4/1987 | Bews et al. | 424/47 |
| 4,775,528 | 10/1988 | Callaghan et al. | 424/66 |
| 5,162,378 | 11/1992 | Guthauser | 514/785 |
| 5,330,751 | 7/1994 | Curtin et al. | 424/66 |
| 5,346,694 | 9/1994 | Juneja | 424/66 |
| 5,534,246 | 7/1996 | Herb et al. | 424/66 |
| 5,676,936 | 10/1997 | Park | 424/65 |

FOREIGN PATENT DOCUMENTS

| | | |
|---|---|---|
| 1068215 | 12/1979 | Canada . |
| 2 048 229 | 12/1980 | United Kingdom . |
| WO 96/19228 | 6/1996 | WIPO . |

OTHER PUBLICATIONS

Michniak–Mikolajczak, An In Vitro Investigation of the Astringency Property of Certain Anhidrotic Solutions, 1985, 37, 141–145, Pol. J. Pharmacol. Pharm.

Michniak, Studies on the mechanism to topical anhidrosis due to polyvalent cations, 1981, 3, 29–36, International Journal of Cosmetic Science.

Primary Examiner—Shelley A. Dodson
Attorney, Agent, or Firm—Stephan P. Williams

[57] ABSTRACT

The present invention embraces antiperspirant compositions with improved efficacy. These compositions contain an aluminum or aluminum-zirconium antiperspirant salt and a water soluble calcium salt, both of which are suspended in a dermatologically acceptable anhydrous carrier vehicle. The present invention also embraces a method of inhibiting or reducing perspiration by topically applying an effective amount of such an antiperspirant composition to the skin.

21 Claims, No Drawings

ANTIPERSPIRANT COMPOSITIONS CONTAINING CALCIUM SALTS

BACKGROUND OF THE INVENTION

The present invention relates to antiperspirant compositions which contain an aluminum or aluminum-zirconium antiperspirant salt and a water soluble calcium salt. It also relates to a method of inhibiting perspiration by topically applying an effective amount of such an antiperspirant composition to the skin.

Antiperspirant compositions containing aluminum or aluminum-zirconium antiperspirant salts are well-known and have been used for many years. There has been an ongoing effort to improve the antiperspirant efficacy of such compositions. Currently the most efficacious antiperspirant compositions contain the so-called "enhanced efficacy" aluminum or aluminum-zirconium antiperspirant salts suspended in an anhydrous carrier. The enhanced efficacy aluminum and aluminum-zirconium antiperspirant salts are well known and are described, for example, in GB 2,048,229 and U.S. Pat. No. 4,775,528. These salts are generally made by heat treating a relatively dilute aqueous solution of the aluminum salt (e.g. about 10% by weight) to increase its HPLC peak 4 to peak 3 ratio, adding zirconium salt if an aluminum-zirconium salt is desired, then spray drying to a powder. These salts typically have an HPLC peak 4 to peak 3 area ratio of 0.7 or higher, with at least 70% of the aluminum contained in said peaks. Beyond using these enhanced efficacy forms of aluminum and aluminum-zirconium salts, however, it has not been possible to provide any significant boost to the efficacy (or sweat inhibition) of present day antiperspirant compositions.

In U.S. Pat. No. 2,571,030 there are disclosed calcium aluminum basic chloride antiperspirant salts which have less of a deteriorating effect on fabric than aluminum basic chloride (chlorhydroxide). These salts are made by reacting calcium carbonate with aluminum chlorhydroxide or with aluminum chloride and aluminum powder, or by adding calcium chloride dihydrate to aluminum chlorhydroxide. This patent suggests that the antiperspirant salts may have 0.2 to 15 parts by weight of calcium for every 100 parts by weight of aluminum. The salts are used in aqueous form to make cream emulsions.

In U.S. Pat. No. 3,979,510 there are disclosed aluminum-zirconium antiperspirant compositions containing aluminum buffering agents to raise the pH. The aluminum buffering agents may include well-known antacid complexes such as hydrated magnesium aluminum sulfate as well as the co-precipitates of aluminum hydroxide with magnesium or calcium carbonate. Examples VIII and XI describe the preparation of Al—Zr salt complexes containing 0.6% and 0.2% calcium respectively. In U.S. Pat. No. 3,996,346 there are disclosed deodorant and antiperspirant compositions which contain zinc oxide and calcium hydroxide, but which do not contain any aluminum salts.

In U.S. Pat. No. 3,998,788 there are disclosed aluminum-zirconium antiperspirant complexes containing trace amounts of alkaline earth metal salts, particularly calcium or magnesium or both, and preferably magnesium. Generally, the complexes will contain one part alkaline earth metal to 30–1000 parts by weight of aluminum plus zirconium. A solution containing 5–15% aluminum plus zirconium (roughly 10 to 30% active) will contain about 0.001–0.1% alkaline earth metal. No composition containing calcium is exemplified.

In U.S. Pat. No. 4,017,599 there are disclosed aluminum-zirconium antiperspirant complexes buffered with salts of amino acids including hydroxy aluminum glycinates and alkaline and alkaline earth glycinates. This patent suggests that the various alkaline salts, including sodium, potassium, ammonium, magnesium and calcium, are equally suitable. Example V of this patent describes a solid aluminum-zirconium hydroxybromide complex containing 2.24% Al, 31.2% Zr, 28.6% Br, 4.26% glycine, and 1.10% Ca. The extremely low Al:Zr ratio of this salt places it well outside the current FDA monograph. In U.S. Pat. No. 4,021,536 there are disclosed astringent zirconium compositions containing a magnesium salt, such compositions having a zirconium to magnesium content, expressed as oxides, of about 30:1 to 1:1. The examples of this patent do not disclose any compositions containing aluminum or calcium.

In CA 1,068,215 there is disclosed a high pay-off antiperspirant stick comprising 5–20% magnesium stearate, 1–5% calcium carbonate, 0–1% mineral oil, 0.1–5% glycine, 0.01–1% deodorant agent, 20–77.8% aluminum chlorhydroxide, 1–10% kaolin, 10–40% rice starch, 0–3% water, and 0.001–1% perfume. The antiperspirant stick is made by making a first blend of the aluminum salt with mineral oil, making a second blend of the rice starch and water, making a third blend of the remaining ingredients, then mixing the three blends and compressing the mixture into a stick.

In WO 96/19228 there are described topical compositions which contain a topical vehicle, a skin irritating ingredient and an anti-irritant amount of an aqueous soluble divalent calcium cation in an amount of 10 mM to 3000 mM. This publication generally suggests a wide variety of topical compositions including sunscreens, insect repellants, shave creams, depilatories, shampoos, permanent wave and hair straightener products, detergents, drug products, antiperspirant and deodorant products, lozenges, mouthwashes, suppositories, etc. No antiperspirant compositions are exemplified, nor is there any suggestion that the efficacy of antiperspirant compositions may be improved by the addition of calcium salts.

In U.S. Pat. No. 5,346,694 there are disclosed antiperspirant compositions in the form of gel sticks which contain a gelling agent stabilizer with a specified $pK_a$. The stabilizer may be a basic metallic salt of certain carboxylic acids. Suitable salt forming cations include sodium, potassium, lithium, magnesium, calcium and zinc. The preferred salts are sodium and potassium benzoate and octanoate. In U.S. Pat. No. 5,534,246 there are disclosed clear water-in-oil antiperspirant emulsions in which the refractive indices of the oil and water phases are matched. A variety of refractive index adjusting compounds are disclosed, one of which is calcium chloride. Examples 5 and 6 disclose aqueous solutions containing, respectively, 32.94% and 36.25% aluminum chlorohydrate and 11.94% and 6.88% calcium chloride.

In U.S. Pat. No. 5,676,936 there are disclosed alcohol based antiperspirant compositions in which the antiperspirant salt is suspended in an alcohol carrier. Prior to addition of the antiperspirant salt, an anti-dissolution agent is incorporated into the alcohol to inhibit dissolution of the antiperspirant salt in the alcohol. The anti-dissolution agent may be a compound having a basic nitrogen function or a basic oxygen function. Compounds having a basic nitrogen function include amino acids. Compounds having a basic oxygen function include inorganic bases such as sodium, potassium, lithium, calcium and magnesium hydroxide.

Michniak, Int'l. J. Cosm. Sci. 3, 29–36 (1981), describes the effect of various polyvalent cations on sweat production using a rat foot pad test. Calcium chloride solution was found to promote sweating. Calcium chloride was also found to reduce the effectiveness of aluminum, lanthanum and zirconium solutions.

It would be highly desirable to provide antiperspirant compositions which are more efficacious—that is, inhibit perspiration to a greater degree—than those compositions which are currently available.

SUMMARY OF THE INVENTION

The present invention embraces antiperspirant compositions with improved efficacy. These compositions contain an aluminum or aluminum-zirconium antiperspirant salt and a water soluble calcium salt, both of which are suspended in a dermatologically acceptable anhydrous carrier vehicle. The present invention also embraces a method of inhibiting or reducing perspiration by topically applying an effective amount of such an antiperspirant composition to the skin.

DETAILED DESCRIPTION OF THE INVENTION

An antiperspirant composition in accordance with the present invention comprises a dermatologically acceptable anhydrous carrier vehicle having suspended therein an aluminum or aluminum-zirconium antiperspirant salt and a water soluble calcium salt. The amount of antiperspirant salt and calcium salt in the composition may be varied within wide parameters, but should be such amount as will effectively inhibit or reduce perspiration—that is, a perspiration reducing effective amount. Generally, the amount of aluminum or aluminum-zirconium antiperspirant salt in the composition will fall within the range of about 5% to about 30% by weight, preferably about 8% to about 25%. The amount of water soluble calcium salt in the composition will typically fall within about 0.5 to about 15% by weight, preferably about 1% to about 12%, and most preferably about 2% to about 9%.

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl in the above formula), especially ⅚ basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ (sometimes written as $Zr(OH)_{4-b}Cl_b$) wherein b is about 1 to 2, preferably about 1.2 to about 1.9. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms, with aluminum-zirconium tetrachlorohydrate being most preferred. Aluminum-zirconium chlorohydrate is referred to as "ACH/ZHC" or as "AZCH" herein. Generally, the aluminum-zirconium antiperspirant salts also contain a neutral amino acid such as glycine, typically in an amount to provide a Zr:Gly ratio of about 1.

The preferred aluminum and aluminum-zirconium salts for use in compositions of the present invention are of the enhanced efficacy type. By "enhanced efficacy salt" is meant an antiperspirant salt which, when reconstituted as a 10% aqueous solution, produces an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Especially preferred are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH" herein. Enhanced efficacy aluminum-zirconium chlorohydrate is referred to as "ACH'/ZHC" or as "AZCH" herein.

Since the most effective antiperspirant salts currently in use are the enhanced efficacy aluminum-zirconium salts, the compositions of the present invention will preferably contain such salts, most preferably enhanced efficacy aluminum-zirconium chlorohydrate. Furthermore, such compositions should ideally contain the maximum amount of such salts that can be reasonably included within FDA guidelines without detracting from the application aesthetics of the final composition. Thus, the composition will ideally contain about 20% to about 25% by weight of the aluminum-zirconium salt (corresponds to about 17–20% active (USP)). However, since aerosol compositions are not currently permitted to contain zirconium, when the compositions of the present invention are formulated as an aerosol, they will preferably contain aluminum chlorohydrate, most preferably enhanced efficacy aluminum chlorohydrate. The amount of antiperspirant salt typically included in aerosol formulations is about 3% to about 15% by weight, preferably about 8% to about 12% by weight.

The antiperspirant composition of the present invention also includes a water soluble calcium salt. By water soluble is meant a salt which has significant solubility in water at room temperature, for example at least 1 gram per 100 ml water, preferably at least 10 grams per 100 ml water, and most preferably at least 25 grams per 100 ml water. Preferred calcium salts include calcium chloride, calcium bromide, calcium nitrate, calcium citrate, calcium formate, calcium acetate, calcium gluconate, calcium ascorbate, calcium lactate, calcium glycinate and mixtures thereof. The more preferred calcium salts are calcium chloride and calcium nitrate, with calcium chloride being most preferred. The amount of water soluble calcium salt in the composition will typically comprise about 0.5% to about 15% by weight of the composition, preferably about 1% to about 12%, and most preferably about 2% to about 9%.

The antiperspirant composition further includes a dermatologically acceptable anhydrous carrier vehicle into which the antiperspirant salt and the calcium salt are suspended. By anhydrous carrier vehicle is meant a vehicle which is substantially free (that is, contains less than 2%, preferably less than 1%, and most preferably less than 0.1% by weight) of free water (that is, excluding any water of hydration associated with the antiperspirant salt). While the carrier may include some lower alkanol, it is preferred that the carrier vehicle is substantially free (that is, contains less than 2%, preferably less than 1%, and most preferably less than 0.1%) of lower alkanol such as ethanol.

The anhydrous carrier vehicle may comprise any of the ingredients commonly utilized in the formulation of topical antiperspirant compositions. Advantageously, the carrier vehicle will comprise one or more silicones. Volatile silicones evaporate quickly and provide a dry feel. The volatile silicones include the cyclic polydimethylsiloxanes, also known as cyclomethicones, which have from about three to about seven silicon atoms, and the linear polydimethylsiloxanes, also known as dimethicones, which have from about 2 to about 8 silicon atoms. The linear volatile silicones generally have viscosities of less than 5 cst, while the cyclic volatile silicones have viscosities under 10 cst. Mixtures of volatile silicones may be advantageously employed.

Non-volatile silicones also can be advantageously included in the carrrier vehicle for their emolliency and application aesthetics. The non-volatile silicones typically have viscosities of about 5 to about 500 cst, preferably 10 to 50 cst, and include polyalkylsiloxanes such as dimethicone and polyalkylarylsiloxanes such as phenyltrimethicone. The non-volatile silicones are generally employed in conjunction with volatile silicones.

The carrier vehicle may also include polyhydric alcohols such as propylene glycol and dipropylene glycol, paraffinic hydrocarbons such as mineral oil and hydrogenated polyisobutene, fatty alcohols such as stearyl alcohol and myristyl alcohol, fatty alcohol esters such as $C_{12-15}$ alcohols benzoate and myristyl octanoate, fatty acid esters such as isopropyl palmitate, myristyl myristate and octyl isononanoate, dicarboxylic acid esters such as diisopropyl sebacate, fatty amides such as Stearamide MEA and Lauramide DEA, polyethylene glycols and polypropylene glycols such as PEG-40 and PPG-20, polyethylene and/or polypropylene glycol ethers of $C_{4-20}$ alcohols such as PPG-10 butanediol, PPG-5-Buteth-7, PPG-3-Myreth-3, and Steareth-20, and polyethylene and/or polypropylene glycol esters of $C_{4-20}$ acids such as PEG-8 Distearate and PEG-10 Dioleate. The vehicle may also include waxes such hydrogenated castor oil (castor wax), gelling agents such as 12-hydroxystearic acid (including esters and amides thereof), glyceryl tribehenate, N-acyl amino acid amides such as N-lauroyl-L-glutamic acid-di-n-butyl amide and alkyl amides such as 2-dodecyl-N,N'-dibutylsuccinamide, suspending agents such as clays (e.g. quaternium-18 hectorite) and silicas, and fillers such as talc, polyolefins and modified corn starch.

The foregoing list of materials is by way of example only and is not intended to be a comprehensive list of all potential materials that may be useful in an antiperspirant composition. Obviously, the skilled worker may select those materials which provide the desired application and aesthetic characteristics of the particular form of antiperspirant composition to be produced. Antiperspirant compositions of the present invention may be readily formulated into topical compositions such as aerosols, pump sprays, liquids, roll-ons, lotions, creams, gels, sticks (both hard and soft), etc.

The present invention also embraces a method of inhibiting or reducing perspiration by topically applying an effective amount of an antiperspirant composition as described herein to the skin of a human, preferably to the axilla, where such reduction in perspiration is desired by the user. An effective amount is that amount which provides at least a 20% sweat reduction, preferably at least a 40% sweat reduction, when tested in accordance with a standard hot room thermal efficacy protocol, and most preferably that amount which reduces perspiration to a degree that is noticeable by the user. Typically, the amount of antiperspirant composition applied will range from about 0.1 gram to about 1.0 gram per axilla depending on the formulation or such amount as will deliver about 0.01 to about 0.25 gram of antiperspirant active per axilla.

The present invention may be further illustrated by the following examples in which the parts and percentages are by weight. In each of these examples, the antiperspirant salts are of the enhanced efficacy type and have an HPLC peak 4 to peak 3 area ratio greater than 0.7 with at least 80% of the aluminum contained in said peaks 3 and 4. In addition, the calcium chloride dihydrate is ground to a fine powder prior to use (e.g. with a Retsch ZM 100 with 0.08 mm sieve and 12 tooth rotor). The compositions with calcium chloride will exhibit improved thermal efficacy compared to a similar composition without calcium chloride.

EXAMPLES 1 TO 5

Liquid Antiperspirant

Liquid antiperspirant compositions are prepared having the ingredients and the amounts set out below. Each of these compositions is prepared by adding all of the ingredients to the cyclomethicone and mixing to form a homogeneous suspension.

| Ingredient | Weight Percent | | | | |
| --- | --- | --- | --- | --- | --- |
| | Ex. 1 | Ex. 2 | Ex. 3 | Ex. 4 | Ex. 5 |
| Cyclomethicone (DC 344) | 74.50 | 73.50 | 66.90 | 60.50 | 59.85 |
| Al—Zr tetrachlorohydrate-gly | 20.00 | 20.00 | 20.00 | 20.00 | |
| Aluminum chlorohydrate | | | | | 23.51 |
| Calcium chloride dihydrate | 1.00 | 2.00 | 8.60 | 15.00 | 8.59 |
| Quaternium-18 hectorite | 3.50 | 3.50 | 3.50 | 3.50 | |
| Propylene carbonate | 1.00 | 1.00 | 1.00 | 1.00 | |
| Talc | | | | | 4.95 |
| Silica | | | | | 3.10 |

EXAMPLES 6 TO 8

Aerosol Antiperspirant

Aerosol antiperspirant compositions are prepared having the ingredients and the amounts set out below. Each of these compositions is prepared by adding all of the ingredients, except the propellant, to the cyclomethicone and mixing to form a homogeneous suspension. The suspension is then placed in an aerosol can and the propellant is added. The propellant is a 1:2 blend of propellants 152A and A31.

| Ingredient | Weight Percent | | |
| --- | --- | --- | --- |
| | Ex. 6 | Ex. 7 | Ex. 8 |
| Cyclomethicone (DC 344) | 24.60 | 26.13 | 23.13 |
| Aluminum chlorohydrate | 9.65 | 9.65 | 9.65 |
| Calcium chloride dihydrate | 3.53 | 2.00 | 5.00 |
| Talc | 2.03 | 2.03 | 2.03 |
| Silica | 1.27 | 1.27 | 1.27 |
| Propellant | 58.92 | 58.92 | 58.92 |

EXAMPLES 9 TO 12

Solid Stick Antiperspirant

Solid stick antiperspirant compositions are prepared having the ingredients and the amounts set out below. Each of these compositions is prepared by mixing all of the ingredients (except the fragrance) with the cyclomethicone, heating the mixture to melt the gelling agents, and cooling the mixture to form a solid stick, with the fragrance being added during the cooling step and prior to solidification.

| | Weight Percent | | | |
|---|---|---|---|---|
| Ingredient | Ex. 9 | Ex. 10 | Ex. 11 | Ex. 12 |
| Cyclomethicone (DC 345) | 41.12 | 36.32 | 46.20 | 48.30 |
| Al—Zr tetrachlorohydrate-gly | 22.68 | 22.68 | 23.50 | 23.50 |
| Calcium chloride dihydrate | 3.50 | 8.30 | 5.70 | 4.40 |
| Stearyl alcohol | 15.53 | 15.53 | 13.50 | 15.20 |
| PPG-10 butanediol | 4.80 | 4.80 | | |
| C12–15 alcohols benzoate | 3.84 | 3.84 | | |
| Hydrogenated castor oil | 2.84 | 2.84 | 3.00 | 3.00 |
| Myristyl myristate | 1.92 | 1.92 | 4.00 | |
| PEG-8 distearate | 0.92 | 0.92 | | 1.00 |
| Silica | | | 1.80 | 1.80 |
| Fragrance | 2.85 | 2.85 | 2.30 | 2.80 |

EXAMPLES 13 TO 15

Cream Antiperspirant

Cream antiperspirant compositions are prepared having the ingredients and the amounts set out below. Each of these compositions is prepared by mixing all of the ingredients, except for the antiperspirant salt, calcium salt, silica, and fragrance, until uniform, heating to 50° C., then mixing under high shear agitation for twenty minutes. The silica is added, mixed until uniform, and the mixture is passed through a Sonolator shear device (Sonic Corp., Model A running at 500 psi through a 0.004 in. diameter orifice) to increase the viscosity. The antiperspirant salt and calcium salt are added and mixed until uniform, then the fragrance is added and mixed until uniform.

| | Weight Percent | | |
|---|---|---|---|
| Ingredient | Ex. 13 | Ex. 14 | Ex. 15 |
| Silicone latex (DC 2-9065) | 54.54 | 54.54 | 54.54 |
| Dimethicone (DC 225) | 10.00 | 10.00 | 9.31 |
| Cyclomethicone (DC 344) | 1.31 | 7.31 | |
| Al—Zr tetrachlorohydrate-gly | 25.00 | 23.50 | 23.50 |
| Calcium chloride (anhydrous) | 6.50 | 2.00 | 10.00 |
| Trihydroxystearin | 0.40 | 0.40 | 0.40 |
| Hydrated Silica (Sylox 2) | 1.00 | 1.00 | 1.00 |
| Fragrance | 1.25 | 1.25 | 1.25 |

Throughout the specification reference to HPLC analysis means that chromatograms of aluminum polymer distribution are obtained as follows: The antiperspirant salt is dissolved in water at about a 10% concentration. A 1.0 µL sample is pumped through a 4.6 mm×50 cm column packed with Nucleosil 100-5 (Keystone Scientific Inc.) using a 0.01M aqueous nitric acid solution as the eluent. The flow rate of the mobile phase is controlled at 0.5 mL/min with a Waters 100 unit. HPLC profiles are recorded and processed with a computerized system that includes the Millennium 2010 Chromatography Manager software from the Millipore/Waters Corp. A Waters 410 differential refractometer is used as the refractive index detector. The HPLC profiles are read from left to right (higher to lower molecular weight). Following this technique, peaks 3 and 4 appear at retention times of Kd=0.32–0.38 and Kd=0.49–0.53 respectively. Naturally, of course, other HPLC techniques which use different column materials, eluents and flow rates can be used provided that they sufficiently resolve peaks 3 and 4 with an acceptable degree of precision (i.e. the technique must be capable of resolving the Al into five distinct peaks). Obviously, such other techniques may place peaks 3 and 4 at different retention times from those given above.

What is claimed is:

1. A topical antiperspirant composition comprising a dermatologically acceptable anhydrous carrier vehicle having suspended therein a perspiration reducing effective amount of an aluminum or an aluminum-zirconium antiperspirant salt and a water soluble calcium salt.

2. The composition of claim 1 wherein said antiperspirant salt comprises about 5% to about 30% by weight of said composition and said calcium salt comprises about 0.5% to about 15% by weight of said composition.

3. The composition of claim 1 wherein said antiperspirant salt comprises about 8% to about 25% by weight of said composition and said calcium salt comprises about 1% to about 12% by weight of said composition.

4. The composition of claim 2 wherein said antiperspirant salt comprises aluminum chlorohydrate or aluminum-zirconium chlorohydrate.

5. The composition of claim 2 or 3 wherein said antiperspirant salt comprises enhanced efficacy aluminum chlorohydrate or enhanced efficacy aluminum-zirconium chlorohydrate.

6. The composition of claim 4 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate and mixtures thereof.

7. The composition of claim 5 wherein said calcium salt is selected from the group consisting of calcium chloride, calcium bromide, calcium nitrate and mixtures thereof.

8. The composition of claim 3 wherein said antiperspirant salt comprises enhanced efficacy aluminum-zirconium chlorohydrate and said calcium salt comprises calcium chloride.

9. The composition of claim 6 wherein said antiperspirant salt has an HPLC peak 4 to peak 3 area ratio of at least 0.7 with at least 80% of the aluminum contained in said peaks 3 and 4.

10. The composition of claim 8 wherein said enhanced efficacy antiperspirant salt has an HPLC peak 4 to peak 3 area ratio of at least 0.7 with at least 80% of the aluminum contained in said peaks 3 and 4.

11. The composition of claim 2, 6 or 9 wherein said carrier vehicle comprises a volatile silicone.

12. The composition of claim 11 wherein said carrier vehicle additionally comprises a non-volatile silicone.

13. The composition of claim 11 in the form of an aerosol, pump spray, liquid, roll-on, lotion, cream, gel, or stick.

14. A method of reducing perspiration from human skin comprising topically applying to human skin a perspiration reducing effective amount of an antiperspirant composition comprising a dermatologically acceptable anhydrous carrier vehicle having suspended therein an aluminum or an aluminum-zirconium antiperspirant salt and a water soluble calcium salt.

15. The method of claim 14 wherein said antiperspirant salt comprises about 5% to about 30% by weight of said composition and said calcium salt comprises about 0.5% to about 15% by weight of said composition.

16. The method of claim 15 wherein said antiperspirant salt comprises enhanced efficacy aluminum chlorohydrate or enhanced efficacy aluminum-zirconium chlorohydrate.

17. The method of claim 16 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate and mixtures thereof.

18. A method of increasing the antiperspirant efficacy of an anhydrous antiperspirant composition comprising an aluminum or an aluminum-zirconium antiperspirant salt, which method comprises adding a water soluble calcium salt to said composition.

19. The method of claim 18 wherein said antiperspirant salt comprises about 5% to about 30% by weight of said composition and said calcium salt comprises about 0.5% to about 15% by weight of said composition.

20. The method of claim 19 wherein said antiperspirant salt comprises enhanced efficacy aluminum chlorohydrate or enhanced efficacy aluminum-zirconium chlorohydrate.

21. The method of claim 20 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate and mixtures thereof.

* * * * *